US008630704B2

(12) United States Patent
Pu et al.

(10) Patent No.: US 8,630,704 B2
(45) Date of Patent: Jan. 14, 2014

(54) NEURAL STIMULATION WITH RESPIRATORY RHYTHM MANAGEMENT

(75) Inventors: Yachuan Pu, Minneapolis, MN (US); Anthony V. Caparso, St. Louis Park, MN (US); Gerrard M. Carlson, Champlin, MN (US); Joseph M. Pastore, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 836 days.

(21) Appl. No.: 11/767,901

(22) Filed: Jun. 25, 2007

(65) Prior Publication Data

US 2008/0319513 A1 Dec. 25, 2008

(51) Int. Cl.
*A61N 1/08* (2006.01)
(52) U.S. Cl.
USPC ........................... 607/2; 607/9; 607/44
(58) Field of Classification Search
USPC ......... 607/11, 18, 20, 27, 42, 44, 45, 46, 2, 7, 607/9, 3–6, 8
See application file for complete search history.

(56) References Cited

U.S. PATENT DOCUMENTS

| | | | | | |
|---|---|---|---|---|---|
| 5,042,497 | A | * | 8/1991 | Shapland | 600/509 |
| 6,021,352 | A | | 2/2000 | Christopherson et al. | |
| 6,076,015 | A | | 6/2000 | Hartley et al. | |
| 6,141,590 | A | * | 10/2000 | Renirie et al. | 607/20 |
| 6,454,719 | B1 | * | 9/2002 | Greenhut | 600/484 |
| 2001/0031990 | A1 | * | 10/2001 | Zhang et al. | 607/4 |
| 2002/0107553 | A1 | * | 8/2002 | Hill et al. | 607/18 |
| 2003/0144709 | A1 | * | 7/2003 | Zabara et al. | 607/46 |
| 2004/0087865 | A1 | | 5/2004 | Kelly | |
| 2004/0111040 | A1 | | 6/2004 | Ni et al. | |
| 2004/0210261 | A1 | | 10/2004 | King et al. | |
| 2004/0215265 | A1 | | 10/2004 | Keizer | |
| 2005/0043644 | A1 | | 2/2005 | Stahmann et al. | |
| 2005/0043772 | A1 | | 2/2005 | Stahmann et al. | |
| 2005/0061320 | A1 | | 3/2005 | Lee et al. | |
| 2005/0113710 | A1 | | 5/2005 | Stahmann et al. | |

(Continued)

FOREIGN PATENT DOCUMENTS

| | | |
|---|---|---|
| AU | 2008269242 B2 | 12/2008 |
| JP | 2004350859 A | 12/2004 |
| WO | WO2006/138069 | 12/2006 |
| WO | WO-2009002402 A1 | 12/2008 |

OTHER PUBLICATIONS

"titration." Merriam-Webster Online Dictionary. 2010. Merriam-Webster Online. May 28, 2010 <http://www.merriam-webster.com/dictionary/titration>.*

(Continued)

*Primary Examiner* — Allen Porter, Jr.
(74) *Attorney, Agent, or Firm* — Schwegman Lundberg & Woessner, P.A.

(57) ABSTRACT

A system embodiment comprises at least one respiration sensor, a neural stimulation therapy delivery module, and a controller. The respiration sensor is adapted for use in monitoring respiration of the patient. The neural stimulation therapy delivery module is adapted to generate a neural stimulation signal for use in stimulating the autonomic neural target of the patient for the chronic neural stimulation therapy. The controller is adapted to receive a respiration signal from the at least one respiration sensor indicative of the patient's respiration, and adapted to control the neural stimulation therapy delivery module using a respiratory variability measurement derived using the respiration signal.

26 Claims, 15 Drawing Sheets

(56) References Cited

U.S. PATENT DOCUMENTS

| | | | |
|---|---|---|---|
| 2005/0209513 | A1 | 9/2005 | Heruth et al. |
| 2005/0222640 | A1* | 10/2005 | Schwartz et al. ............... 607/44 |
| 2005/0251218 | A1* | 11/2005 | Markowitz et al. ............. 607/17 |
| 2005/0261741 | A1* | 11/2005 | Libbus et al. ..................... 607/3 |
| 2006/0282131 | A1 | 12/2006 | Caparso et al. |
| 2007/0073181 | A1 | 3/2007 | Pu et al. |
| 2007/0129769 | A1 | 6/2007 | Bourget et al. |

OTHER PUBLICATIONS

Bradley, T. D., et al., "Continuous positive airway pressure for central sleep apnea and heart failure", *N Engl J Med.*, 353(19), (2005),2025-33.

Fallen, E. L., "Vagal afferent stimulation as a cardioprotective strategy? Introducing the concept", *Ann Noninvasive Electrocardiol.*, 10(4), (Oct. 2005),441-6.

Groves, D. A., et al., "Vagal nerve stimulation: a review of its applications and potential mechanisms that mediate its clinical effects.", *Neurosci Biobehav Rev.*, 29(3), (2005), 493-500.

Henry, T. R., et al., "Therapeutic mechanisms of vagus nerve stimulation", *Neurology*, 59(6 Suppl 4), (2002),S3-14.

Holmes, M. D., et al., "Vagal nerve stimulation induces intermittent hypocapnia", *Epilepsia*, 44(12), (2003),1588-91.

Kowallik, P., et al., "Breath-to-breath variability correlates with apnea-hypopnea index in obstructive sleep apnea", *Chest*, 119(2), (2001),451-9.

Lee, Kent, et al., "Method and Apparatus for Controlling Neural Stimulation During Disordered Breathing", U.S. Appl. No. 11/468,603, filed Aug. 30, 2006.

Marzec, M., et al., "Effects of vagus nerve stimulation on sleep-related breathing in epilepsy patients", *Epilepsia*, 44(7), (Jul. 2003),930-5.

Rostig, S., et al., "Nonrandom variability of respiration during sleep in healthy humans", *Sleep*, 28(4), (2005),411-7.

Zaaimi, B., et al., "Vagus nerve stimulation induces concomitant respiratory alterations and a decrease in SaO2 in children.", *Epilepsia*, 46(11), (2005), 1802-9.

"International Application Serial No. PCT/US2008/007307, International Search Report mailed Oct. 6, 2008", 4 pgs.

"International Application Serial No. PCT/US2008/007307, Written Opinion mailed Oct. 6, 2008", 8 pgs.

"Australian Application Serial No. 2008269242, First Examiner Report mailed Oct. 12, 2010", 3 Pgs.

"Japanese Application Serial No. 2010-513195, Office Action mailed Aug. 21, 2012", 2 pgs.

"Japanese Application Serial No. 2010-513195, Response filed Apr. 18, 2012 to Office Action mailed Jan. 18, 2012", English Claims with response, 11 pgs.

"Australian Application Serial No. 2008269242, Request to Amend a Complete Specification and First Statement of Proposed Amendments filed May 16, 2011", 16 pgs.

"European Application Serial No. 08768362.9, Office Action mailed Feb. 9, 2010", 2 pgs.

"European Application Serial No. 08768362.9, Response filed Mar. 4, 2010 to Office Action mailed Feb. 9, 2010", 12 pgs.

"Japanese Application Serial No. 2010-513195, Office Action Mailed Jan. 18, 2012", 8 pgs.

"Japanese Application Serial No. 2010-513195, Response filed Jan. 8, 2013 to Office Action mailed Aug. 17, 2012", With English Claims, 9.

\* cited by examiner

NEURAL STIMULATION WITH RESPIRATORY RHYTHM MANAGEMENT

TECHNICAL FIELD

This application relates generally to medical devices and, more particularly, to systems, devices and methods for delivering neural stimulation.

BACKGROUND

The autonomic nervous system has been stimulated to modulate various physiologic functions, such as cardiac functions and hemodynamic performance. The myocardium is innervated with sympathetic and parasympathetic nerves. Activities in these nerves, including artificially applied electrical stimuli, modulate the heart rate and contractility (strength of the myocardial contractions). Neural stimulation that elicits a parasympathetic response (e.g. stimulating nerve traffic at a parasympathetic neural target such as a cardiac branch of the vagus nerve and/or inhibiting nerve traffic at a sympathetic neural target) is known to decrease the heart rate and the contractility, lengthen the systolic phase of a cardiac cycle, and shorten the diastolic phase of the cardiac cycle. Neural stimulation that elicits a sympathetic response (e.g. stimulating nerve traffic at a sympathetic neural target and/or inhibiting nerve traffic at a parasympathetic neural target) is known to have essentially the opposite effects. The ability of the electrical stimulation of the autonomic nerves in modulating the heart rate and contractility may be used to treat abnormal cardiac conditions, such as to improve hemodynamic performance for heart failure patients and to control myocardial remodeling and prevent arrhythmias following myocardial infarction. The autonomic nervous system regulates functions of many organs of the body. Vagus nerve stimulation, for example, affects respiration as the vagus nerve includes many lung, bronchial and tracheal afferents that feed into the respiratory centers of the brainstem.

SUMMARY

This disclosure relates to systems, devices methods for monitoring respiration to improve the efficacy of a neural stimulation therapy and/or reduce or avoid side effects of a neural stimulation therapy. Respiration changes during sleep or rest, a state with a predominant vagal/parasympathetic activity and stabilized respiration, are used to titrate the neural stimulation therapy. Various embodiments use a measurement of respiratory stability or instability during sleep or rest as a feedback to control stimulation of an autonomic neural target (e.g. vagus nerve stimulation). Various embodiments use a measurement of variability of a respiratory parameter, such as respiratory rate, as an indicator of respiratory stability or instability. A decrease in respiratory variability is a sign of improvement, and an increase in respiratory variability is a sign of disease progression.

A system embodiment comprises at least one respiration sensor, a neural stimulation therapy delivery module, and a controller. The respiration sensor is adapted for use in monitoring respiration of the patient. The neural stimulation therapy delivery module is adapted to generate a neural stimulation signal for use in stimulating the autonomic neural target of the patient for the chronic neural stimulation therapy. The controller is adapted to receive a respiration signal from the at least one respiration sensor indicative of the patient's respiration, and adapted to control the neural stimulation therapy delivery module using a respiratory variability measurement derived using the respiration signal.

According to a method embodiment, a chronic neural stimulation therapy is delivered. The therapy includes stimulation to an autonomic neural target. Respiration is monitored during a low activity period. Respiration variability is determined using the monitored respiration. An intensity of the stimulation to the autonomic neural target is adjusted using a comparison the respiration variability to at least one predetermined threshold.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
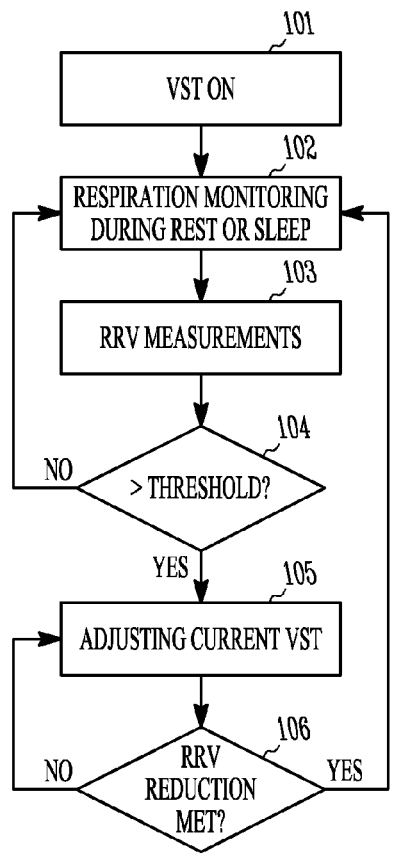
FIG. 1 illustrates an embodiment of a method for delivering neural stimulation with respiratory rhythm feedback.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments use a measurement of respiratory stability or instability as a feedback to control stimulation of an autonomic neural target (e.g. vagus nerve stimulation). Various embodiments use a measurement of variability of a respiratory parameter as an indicator of respiratory stability or instability. Various embodiments use respiration rate variability (RRV) or tidal volume variability (TVV) as an indicator of respiratory stability or instability. Changes in respiration (patterns or rates) reflect an underlying therapy benefit or pathological process. A decrease in respiratory variability is a sign of improvement, and an increase in respiratory variability is a sign of disease progression. For example, some embodiments use a measure of variability of a respiratory parameter (e.g. rate, tidal volume, an inspiratory/expiratory ratio, etc.) during sleep or a rest state to adjust a chronic vagus nerve therapy. The neural stimulation intensity can be adjusted to reduce the mean of the monitored respiratory parameter, or reduce the variability of the monitored respiratory parameter, or reduce both the mean and variability of the monitored respiratory parameter. Various embodiments provide a respiration monitor to improve the efficacy of vagus nerve stimulation and/or reduce or avoid undesired side effects, such as a breathing disorder. The present subject matter monitors respiration changes during sleep and/or rest, which is a state with a predominant vagal/parasympathetic activity, and with stabilized respiration.

Various stimulator embodiments include at least one respiration sensor adapted for use in monitoring respiration of the patient, a neural stimulation therapy delivery module adapted to generate a neural stimulation signal for use in stimulating the autonomic neural target of the patient for the chronic neural stimulation therapy, and a controller adapted to receive a respiration signal from the at least one respiration sensor indicative of the patient's respiration, and adapted to control the neural stimulation therapy delivery module using a respiratory variability measurement derived using the respiration signal. Various embodiments include a respiration variability analyzer adapted to determine the respiration variability measurement using the respiration signal, a titration detector adapted to deliver a control signal to control a therapy intensity using the respiration variability measurement from the respiration variability analyzer, and a safety detector adapted to compare the respiration variability measurement from the respiration variability analyzer to a threshold and deliver a control signal to control a therapy intensity based on the comparison. The respiration sensor and the controller are adapted to monitor respiration during a period of low activity, and the controller is adapted to control the neural stimulation delivery module using a respiratory variability measurement corresponding to the period of low activity. The period of low activity can be a period of sleep or rest, such as may be detected by an activity detector. A predetermined schedule can be used to anticipate periods of low activity.

Various embodiments deliver a chronic neural stimulation therapy to an autonomic target. The term chronic indicates a period of time on the order of days, weeks, months or years. Chronic therapy includes therapy with intermittent stimulation and therapy with and constant stimulation. Respiration is monitored during a low activity period, and respiration variability is determined. An intensity of the stimulation to the autonomic neural target is adjusted using a comparison of the respiration variability to at least one predetermined threshold, such as a titration threshold indicative of an efficacy of the simulation for the therapy and/or a side effect threshold indicative of an undesired side effect of the stimulation. Various embodiments include identifying a patient indicated for a particular therapy, and delivering the therapy, such as a heart failure therapy, a hypertension therapy, or a post myocardial infarction therapy. A footprint representative of the respiration variability can be generated, along with one or more indices representative of quantitative measurements of the footprint. Examples of indices include a feature, a pattern, a shape or a contour of the footprint.

Embodiments of the present subject matter include cardiac, renal neuromodulation and other therapeutic devices for patient populations, such as heart failure, post myocardial infarction, and hypertension. Respiration provides an early marker (respiration) for the efficacy of vagal nerve stimulation, or other therapies that affect the autonomic balance of a patient (such as therapies for heart failure, post myocardial infarction, and hypertension). Respiration can also be used to detect undesired side effects, such as predetermined breathing disorders.

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force is increased when the sympathetic nervous system is stimulated, and is decreased when the sympathetic nervous system is inhibited (the parasympathetic nervous system is stimulated). An afferent nerve conveys impulses toward a nerve center. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intention, increases urine secretion, and contracts the wall and relaxes the sphincter of the bladder. The functions associated with the sympathetic and parasympathetic nervous systems are many and can be complexly integrated with each other.

Vagal modulation may be used to treat a variety of disorders, including a variety of cardiovascular disorders, including heart failure, post-MI remodeling, and hypertension. These conditions are briefly described below.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Respiration, as can be quantified or measured using a respiratory rate, tidal volume and the like, demonstrates a non-randomness with small variability among normal people especially during sleep. More than 50% of heart failure patients experience central sleep apnea or periodic breathing. Respiratory instability, such as can be measured by the ratio of minute ventilation to minute production of carbon dioxide (VE/VCO2) or the like, can be attributed to sympathetic elevation as well as cardiac dysfunction. It has been observed that heart failure and breathing disorders are associated. For example, an association was observed between improving heart failure and reducing respiration rate/variability, as well as worsening heart failure and increasing respiration rate/variability. This observation agrees with a long-lasting intuitive belief that respiration and heart are connected.

FIG. 1 illustrates an embodiment of a method for delivering neural stimulation with respiratory rhythm feedback. As illustrated at 101, a neural stimulation therapy, such as a vagal stimulation therapy (VST), is delivered. The VST can be a chronic stimulation therapy, such as a therapy for heart failure, post-MI remodeling, and hypertension. The present subject matter can also be used with other chronic autonomic nerve stimulation therapies, such a therapies for epilepsy, eating disorders, migraines and pain, by way of example and not limitation. At 102, respiration is monitored during a period of sleep or rest (a period of a predominant parasympathetic activity and stable respiration). Respiration can be monitored using a variety of techniques, such as through the use of transthoracic impedance. Examples of respiration parameters that can be monitored include respiratory rate (RR) and tidal volume (TV). The respiration monitor can use minute ventilation, breath-breath interval, tidal volume and the like. As illustrated at 103, the monitored respiration is used to measure a respiration variability using the monitored respiration. For example, a respiration rate variability (RRV) can be calculated using a monitored respiration rate, and a tidal volume variability (TVV) can be calculated using a monitored tidal volume. At 104, the variability measurement is compared to a predetermined threshold value. If the measurement is greater than a threshold, the neural stimulation therapy (e.g. VST) is adjusted to improve the variability as illustrated at 105. For example, if the RRV is higher than a threshold, the intensity of the neural stimulation is adjusted to lower the RRV until a desired RRV reduction is observed, as illustrated at 106.

Figure 2:
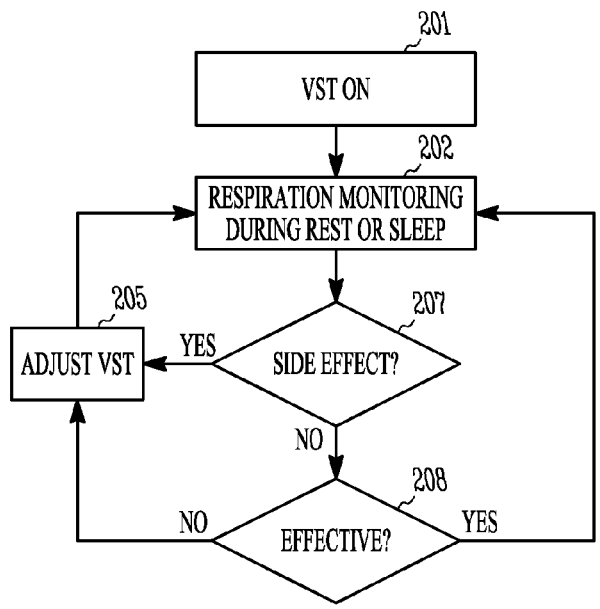
FIG. 2 illustrates an embodiment of a method for delivering neural stimulation with respiratory rhythm feedback to both titrate the therapy and avoid or abate predetermined undesired side effects.

FIG. 2 illustrates an embodiment of a method for delivering neural stimulation with respiratory rhythm feedback to both titrate the therapy and avoid or abate predetermined undesired side effects. As illustrated at 201 in the figure, a neural stimulation therapy, such as a vagal stimulation therapy (VST), is delivered. Respiration is monitored at 202 during a state with predominate parasympathetic activity and stable respiration, such as states of sleep or rest. A clock and a preprogrammed schedule can be used to estimate times of sleep. Activity/posture sensors may also be used to determine states of rest. Apnea may be detected, the mean rate and standard deviation can be calculated, and a respiration variability footprint can be created. At 207, it is determined whether undesired side effects have been detected. For example, a minute ventilation signal can be used to detected prolonged absence of breathing, a high apnea-hypopnea index (AHI) or other index for respiratory disturbance, and large variability in respiration as indicated by a large standard deviation or respiration variability footprint. Parameter(s) of the VST can be adjusted to appropriate adjust the intensity of the therapy, as illustrated at 205, if an undesired side effect is detected. The effectiveness of the VST is determined at 208. An improved efficacy of the vagal stimulation therapy can be indicated by a reduction in variability (every hour or day, for example). If the efficacy of the VST is not at or above a threshold value, the VST intensity is adjusted at 205. The stimulation parameter(s) can be adjusted automatically the implantable stimulator in a close-loop therapy. The stimulation parameter(s) can be adjusted by a physician using a programmer or using an advanced patient management system. Examples of stimulation parameter(s) that can be adjusted to adjust the VST intensity include one or various combinations of an amplitude, frequency, and pulse width of the signal. Also, the duration, duty cycle and schedule of the stimulation can be adjusted to titrate the VST.

Figure 3:
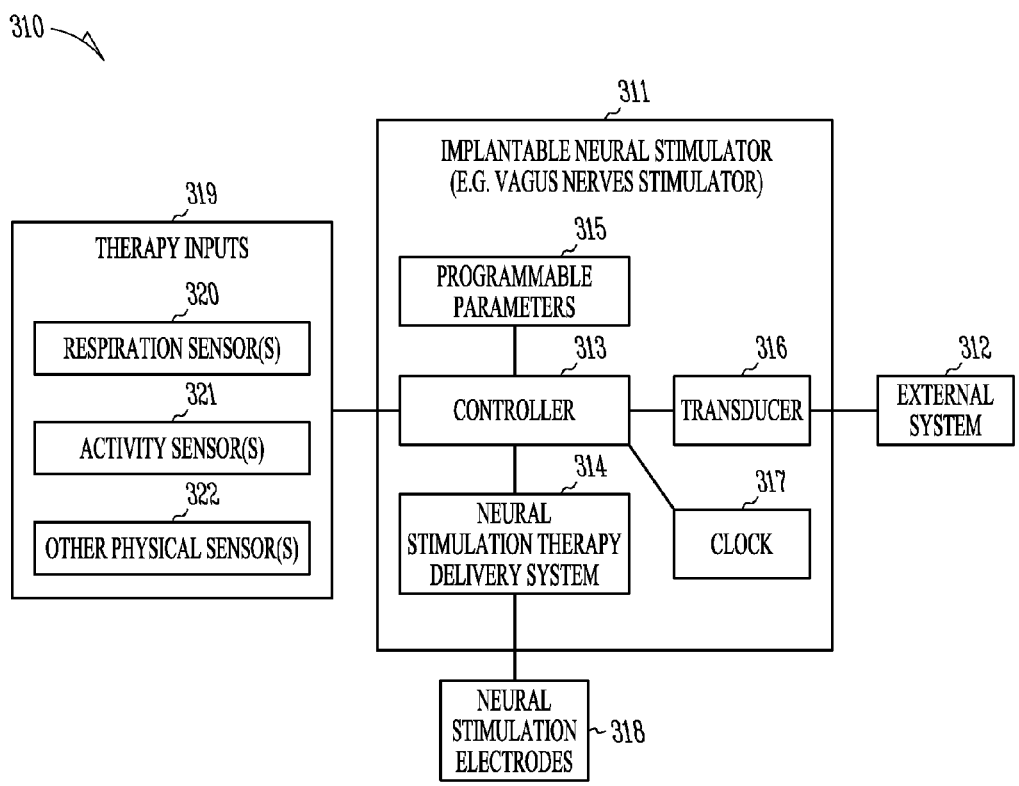
FIG. 3 illustrates a neural stimulation system with respiratory variability management, according to various embodiments.

FIG. 3 illustrates a neural stimulation system with respiratory variability management, according to various embodiments. The illustrated system 310 includes an implantable neural stimulator 311, such as a vagus nerve stimulator, and further includes an external system 312. The external system 312 and implantable stimulator 311 are adapted to communicate with each other. The external system can include a programmer. The external system can include one or more devices that form an advanced patient management system. The illustrated stimulator 311 includes a controller 313, a neural stimulation therapy delivery system 314, and programmable parameter(s) 315 used in delivering a neural stimulation therapy using the neural stimulation therapy delivery system. The illustrated device includes a transducer 316, through which the illustrated stimulator embodiment wirelessly communicates with the external system. A clock 317 can be used by the controller to implement preprogrammed therapy schedules. The controller 313 controls the neural stimulation therapy delivery system 314 to deliver neural stimulation to a neural target through neural stimulation electrode(s) 318 or using transducers such as transducers that deliver neural stimulation using ultrasound, thermal, light and magnetic energy. Examples of electrodes include nerve cuff electrodes adapted to stimulate a vagus nerve or other neural target, and intravascularly-placed electrodes adapted to transvascularly stimulate a neural target, such as electrodes adapted to be fixed within an internal jugular vein to transvascularly stimulate a vagus nerve.

Also, as illustrated in the FIG. 3, the system 310 includes therapy input(s) 319, including inputs from respiration sensor(s) 320. Other therapy inputs can include activity sensors 321 and other physiologic sensors 322 such as heart rate sensors, sensors to detect cardiograms, and blood pressure sensors, for example. These therapy inputs can be from an internal sensor connected, either through a lead or wirelessly, to the implantable stimulator, and/or can be from external sensors or other external sources. The respiration sensor(s) 320 are used to develop a respiratory variability parameter such as RRV or TVV. Some embodiments determine RRV, for example, internal to the implantable neural stimulator, and some embodiments determine RRV using the external system. Programmable parameter(s) 315 can be adjusted using the determined respiratory variability, such that the neural stimulation therapy delivered using the controller 313 and system 314 is adjusted based on the respiratory variability.

Figure 4:
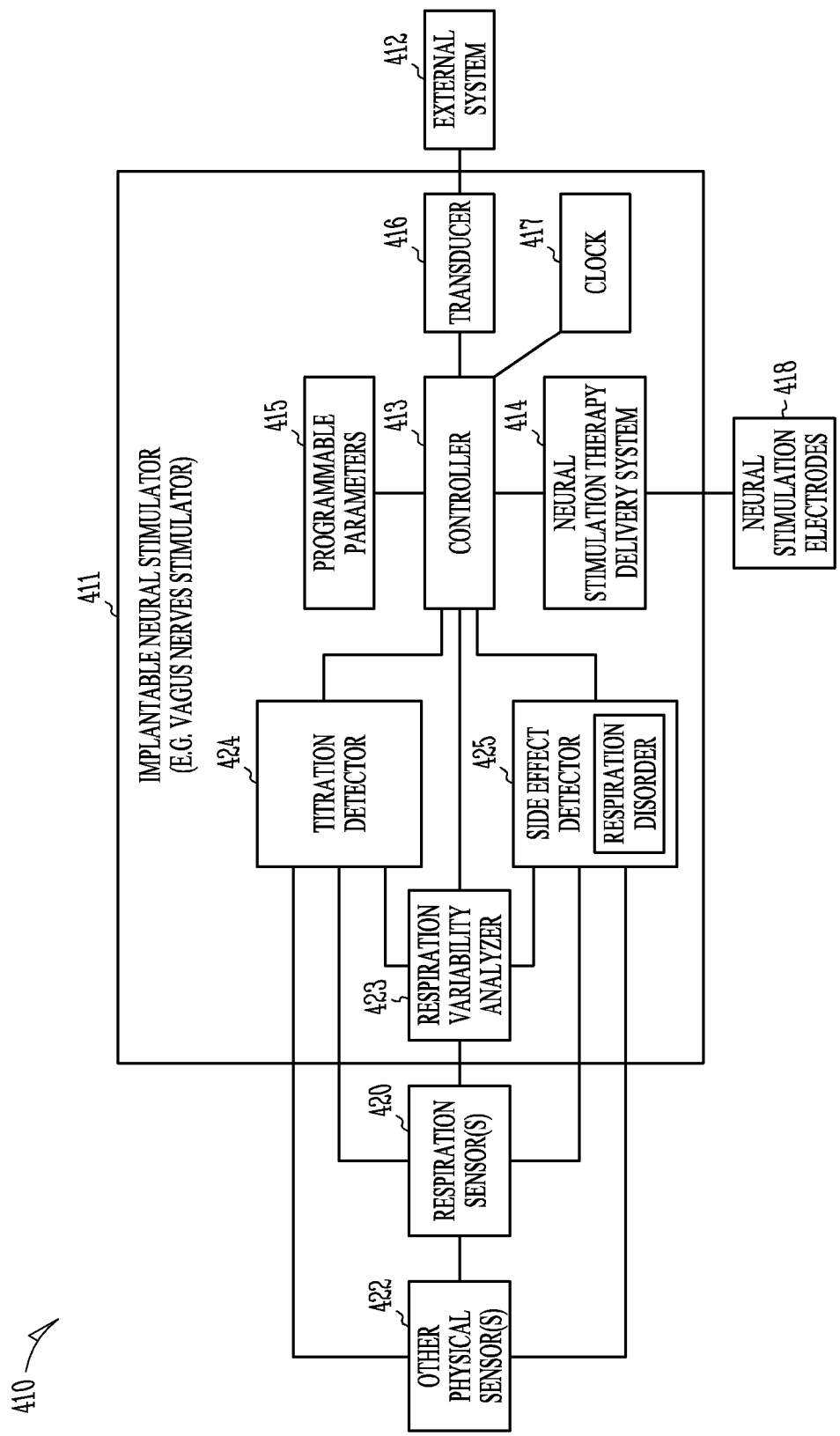
FIG. 4 illustrates a neural stimulation system with respiratory variability management, according to various embodiments.

FIG. 4 illustrates a neural stimulation system with respiratory variability management, according to various embodiments. The illustrated system 410 includes an implantable neural stimulator 411, such as a vagus nerve stimulator, and further includes an external system 412. The external system 412 and implantable stimulator 411 are adapted to communicate with each other. The illustrated stimulator 411 includes a controller 413, a neural stimulation therapy delivery system 414, and programmable parameter(s) 415 used in delivering a neural stimulation therapy using the neural stimulation therapy delivery system. The illustrated device includes a transducer 416, through which the illustrated stimulator embodiment wirelessly communicates with the external system. A clock 417 can be used by the controller to implement preprogrammed therapy schedules. In the illustrated system, the controller 413 controls the neural stimulation therapy delivery system 414 to deliver neural stimulation to a neural target through neural stimulation electrode(s) 418.

The illustrated implantable neural stimulator 411 is adapted to internally-process the therapy inputs, including internally determine a respiration variability. As shown in FIG. 4, the stimulator 411 includes a respiration variability analyzer 423 adapted to receive a signal from respiration sensor(s) 420 indicative of a respiration parameter or parameters, and further adapted to determine a respiration variability using the signal from the respiration sensor(s). For example, some embodiments derive respiration rate information using the signal from the respiration sensor(s), and determine a RRV using the respiration variability analyzer. Some embodiments determine TVV using the signal from the respiration sensor(s). Variability can be determined using other respiration parameters. The controller 413 can receive a signal representative of the respiration variability from the analyzer 423, appropriately adjust the programmable parameter(s), and adjust the intensity of the neural stimulation therapy delivered using the therapy delivery system 414.

The illustrated implantable neural stimulator 411 includes a titration detector 424 adapted for use in detecting an indicator for an efficacy of the neural stimulation therapy, and further includes a side effect detector 425 for use in detecting an indicator of an undesired side effect of the neural stimulation therapy. According to various embodiments, the titration detector 424 can use a signal from the respiration variability analyzer 423, a signal from the respiration sensor(s), and/or a signal from other physiologic sensor(s) 422 such as heart rate sensors, blood pressure sensors, chemical sensors, electrogram sensors, and the like. Some embodiments compare monitored respiratory variability footprints or indices to predetermined respiration variability footprints or indices to determine whether the neural stimulation therapy is effective whether to adjust the intensity of the neural stimulation therapy.

According to various embodiments, the side effect detector 425 can use a signal from the respiration variability analyzer 423, a signal from the respiration sensor(s), and/or a signal from other physiologic sensor(s) 422 such as heart rate sensors, blood pressure sensors, chemical sensors, electrogram sensors, and the like. The illustrated side effect detector includes a detector of predetermined respiratory disorder(s) such as a prolonged absence of breathing, a high apnea-hypopnea index (AHI) or other index for respiratory disturbance. Some embodiments use predetermined respiration variability footprints or indices to determine predetermined side effects. Some embodiments also detect undesired side effects using other physiologic sensors such as heart rate and cardiograms.

Figure 5:
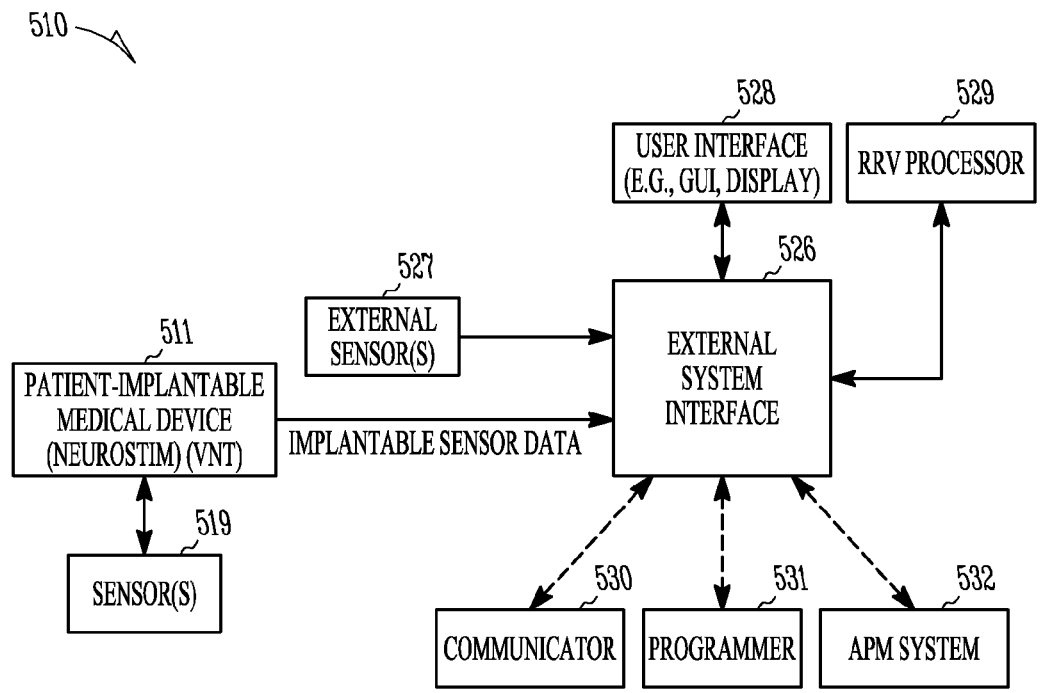
FIG. 5 illustrates a system embodiment for managing neural stimulation therapy using a respiratory rate (RRV) footprint and associated indices.

FIG. 5 illustrates a system embodiment for managing neural stimulation therapy using an RRV footprint and associated indices. The illustrated system 510 includes a patient-implantable medical device 511, such as a neural stimulation device adapted to deliver a vagal stimulation therapy (VST). The device 511 incorporates or is coupled to one or more implantable sensors 519. One or more of the sensors 519 are configured to sense a respiration parameter of the patient's breathing. Respiratory information can be obtained using one or more sensors, such as an implantable sensor(s), or a patient-external sensor(s), or combinations of implantable and external sensors. Examples of respiration sensors include a minute ventilation sensor, transthoracic impedance sensor, accelerometer, or other sensor capable of producing a respiration waveform representative of the patient's breathing such as a pressure sensor, cardiac sensor (e.g. ECG sensor), electromyogram sensor, and an airflow sensor (e.g. positive airway pressure device or ventilator). Other sensors, such as a pulse oximetry sensor, blood pressure sensor, patient temperature sensor, and EKG sensor, may also be used to sense various physiological parameters of the patient.

The illustrated system 510 includes a number of patient-external devices. An external system interface 526 includes communication circuitry configured to effect communications with implantable device 511. The external system interface 526 may also be configured to effect communications with external sensors 527. The external system interface may be communicatively coupled to, or integral with, one or more of a programmer, an advanced patient management system, a portable or hand-held communicator, or other patient-external system. The external system interface 526 is coupled to a user interface 528, such as a graphical user interface or other interface that provides a display. The user interface 528 can include a user actuatable input/output device, such as a keyboard, touch screen sensor, mouse, light pen, and the like. The user interface may be used to input therapy information, such programming a schedule, and programming stimulation parameters that can effect an intensity for the neural stimulation therapy. The system 510 includes a respiration variability processor 529, illustrated as an RRV processor, coupled to the external system interface. The RRV processor may be incorporated as a component of the implantable device 511, a communicator 530, a programmer 531, or an advanced patient management (APM) system 532. The respiration variability processor determines respiratory variability (e.g. an RRV footprint and indices developed from the RRV footprint). This and other relevant information can be communicated to the external system interface 526 for display to the physician, clinician, and/or patient.

Figure 6:
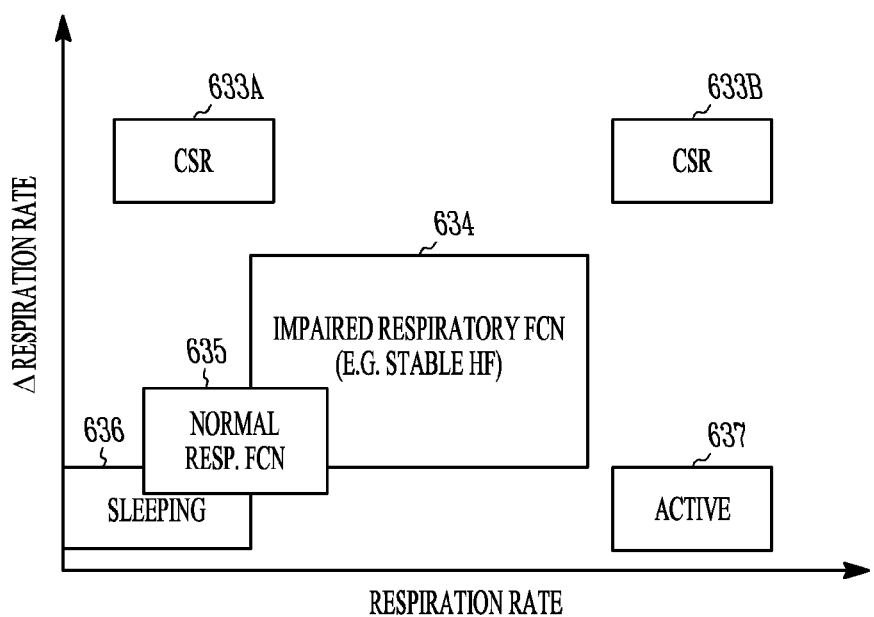
FIG. 6 illustrates a mapping of regions of interest associated with an RRV footprint.

FIG. 6 illustrates a mapping of regions of interest associated with an RRV footprint. These regions represent characterizations of patient status or condition based on a clinical appreciation of how RRV footprint characteristics correspond with patient status or condition. For example, the presence of islands within regions 633A and 633B indicates the presence of Cheyne-Stokes Respiration. An increase in footprint area within region 634 indicates an increase in impaired respiratory function (e.g., stable heart failure). An increase in footprint area within region 635 indicates an increase in normal respiratory function. An increase in footprint area within region 636 is an indication of patient sleep, while an increase in footprint area within region 637 is an indication of increased patient activity. The mapping illustrated in FIG. 6 provides a generalized "guide" to interpreting an RRV footprint. Regions, patterns, features, and other aspects of an RRV footprint may be visually (manually) or algorithmically analyzed based on such a guide or map to facilitate manual or automatic interpretation and quantification of an RRV footprint. Variability mappings can be calculated for other respiratory parameters (e.g. a map for tidal volume variability).

FIGS. 7A, 7B, 8A, 8B, 9 and 10 illustrate RRV footprints. The illustrated RRV footprints shown in the figures are color coded to indicate a third-dimension in addition to the two-dimensional RRV footprint. Such coloring of contour lines is not shown in the black and white rendering of the application drawings, but rather the colors are identified by labels in parentheses in FIGS. 9 and 10. As discussed further below, the different colors indicate differences in the parameter that defines the third dimension.

Figure 7B:
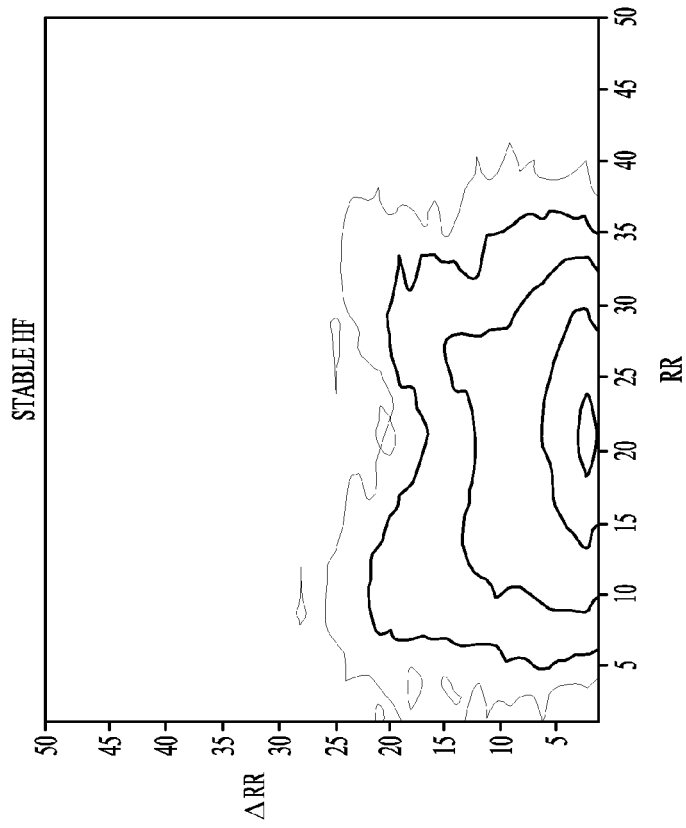
FIG. 7B shows an RRV footprint for a stable heart failure patient.
Figure 7A:
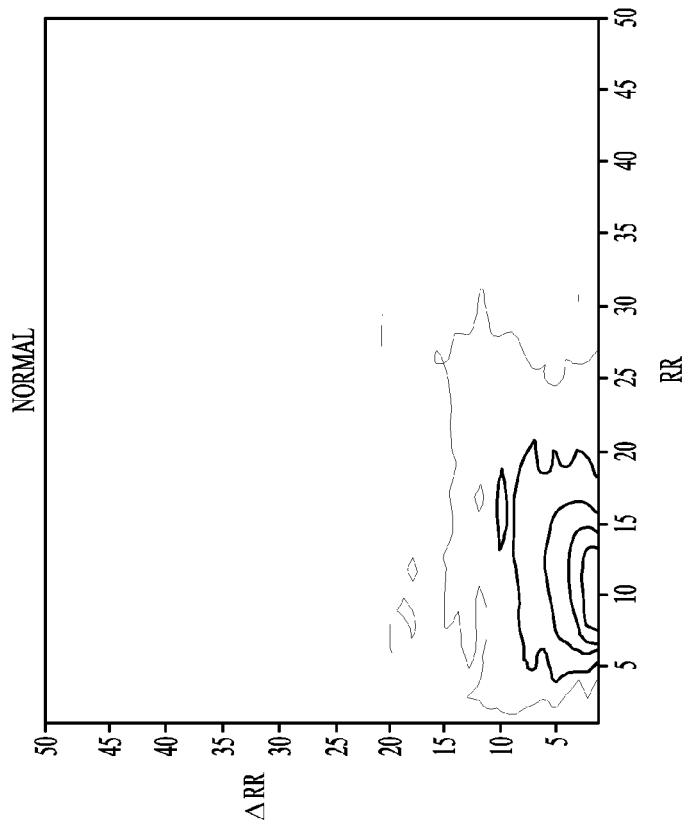
FIG. 7A shows an RRV footprint for a normal subject.

FIG. 7A shows an RRV footprint for a normal subject. The RRV footprint is centered around 10 breaths per minute (br/m) and the contour is confined and smooth. FIG. 7B shows an RRV footprint for a stable heart failure patient. The RRV footprint in FIG. 7B, as compared to that of FIG. 7A, is shifted to the right, indicative of a higher respiratory rate (RR). The footprint of FIG. 7B also has a wider range of RR and ΔRR. The contour of the footprint of FIG. 7B is still relatively smooth. RRV footprints that show increased area and movement to the right (e.g., higher RR) are generally indicative of a worsening heart failure status.

Figure 8B:
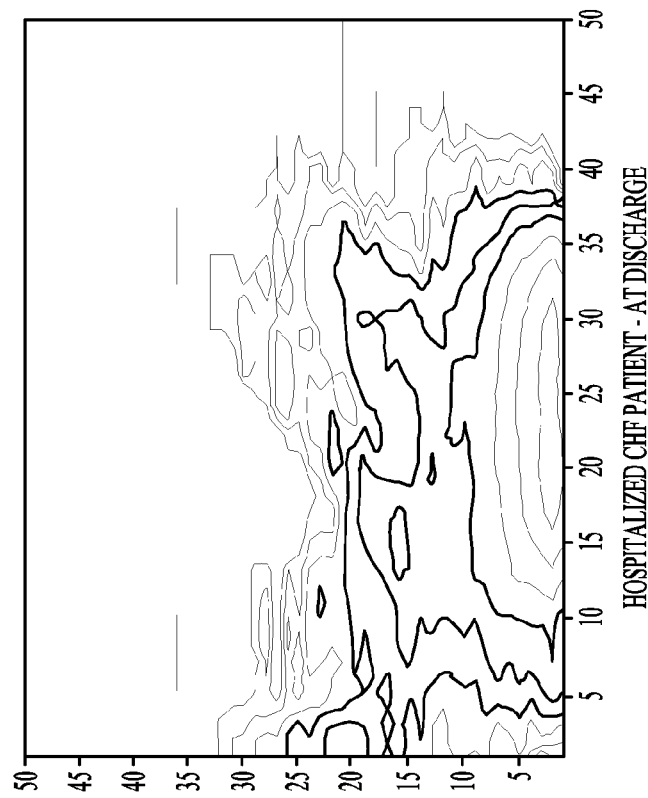
FIG. 8B shows an RRV footprint for the same heart failure patient at discharge, and indicates an improved heart failure status of the patient.
Figure 8A:
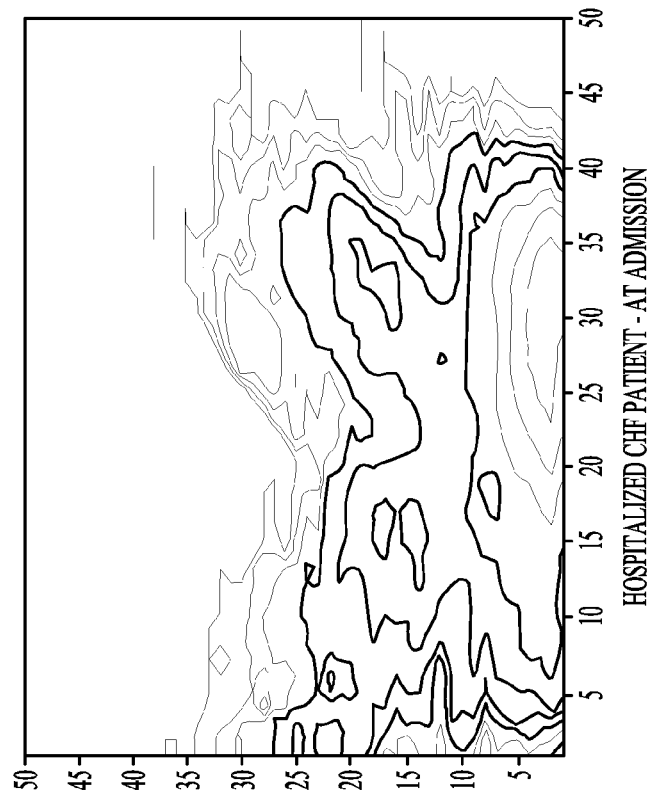
FIG. 8A shows an RRV footprint for a hospitalized heart failure patient at admission.

FIG. 8A shows an RRV footprint for a hospitalized heart failure patient at admission. FIG. 8B shows an RRV footprint for the same heart failure patient at discharge, and indicates an improved heart failure status of the patient. The RRV footprint for the patient at admission shown in FIG. 8A is significantly drifted to the right, has a large footprint area with extremely irregular contour, and many isolated islands indicative of abnormal breathing patterns, periodic breathing in this case. The RRV footprint at discharge, shown in FIG. 8B, is less shifted to the right than in FIG. 8A, and has a large footprint but with limited isolated islands, indicating an improvement in periodic breathing.

Figure 9:
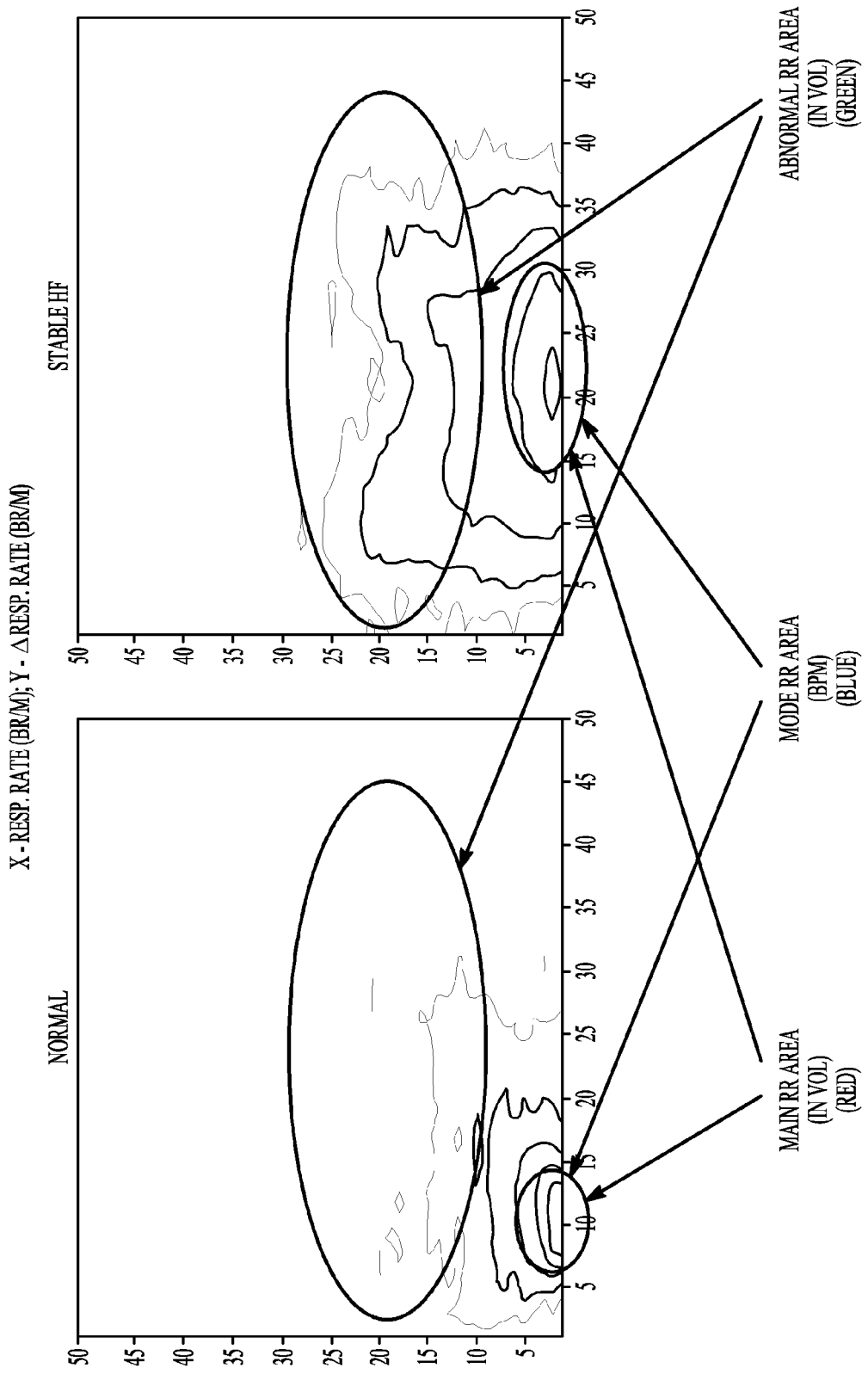
FIG. 9 shows an RRV footprint for a normal patient next to an RRV footprint for a stable heart failure patient.

FIG. 9 shows an RRV footprint for a normal patient next to an RRV footprint for a stable heart failure patient. As illustrated in FIG. 9, various regions of the footprints can be colored, and annotation may be added (e.g., arrows, ovals, and corresponding descriptors) to accentuate portions of the footprints of particular interest. In the illustrated example, the different colors of the contour lines correspond to a different frequency of occurrence, with red representing highest occurrence and green lowest occurrence. In the illustrated example, a red region of the footprint denotes the main RR area, a blue region denotes the mode of RR in br/m, and the green region denotes abnormal RR area. The figure shows differences in each color encircled region depending on the heart failure status of the patient. Such differences include the location, area, and/or shape of each color-encircled region. For example, the RRV footprint for the stable heart failure patient shows a significant shift to the right in the mode of RR (blue arrow point) and significant enlargement of both the main RR area (red circled region) and abnormal RR area (green circled region) relative to the RRV footprint for a normal patient. The magnitude of differences between the two footprints is reflective of a change in the heart failure status of the patient.

Figure 10:
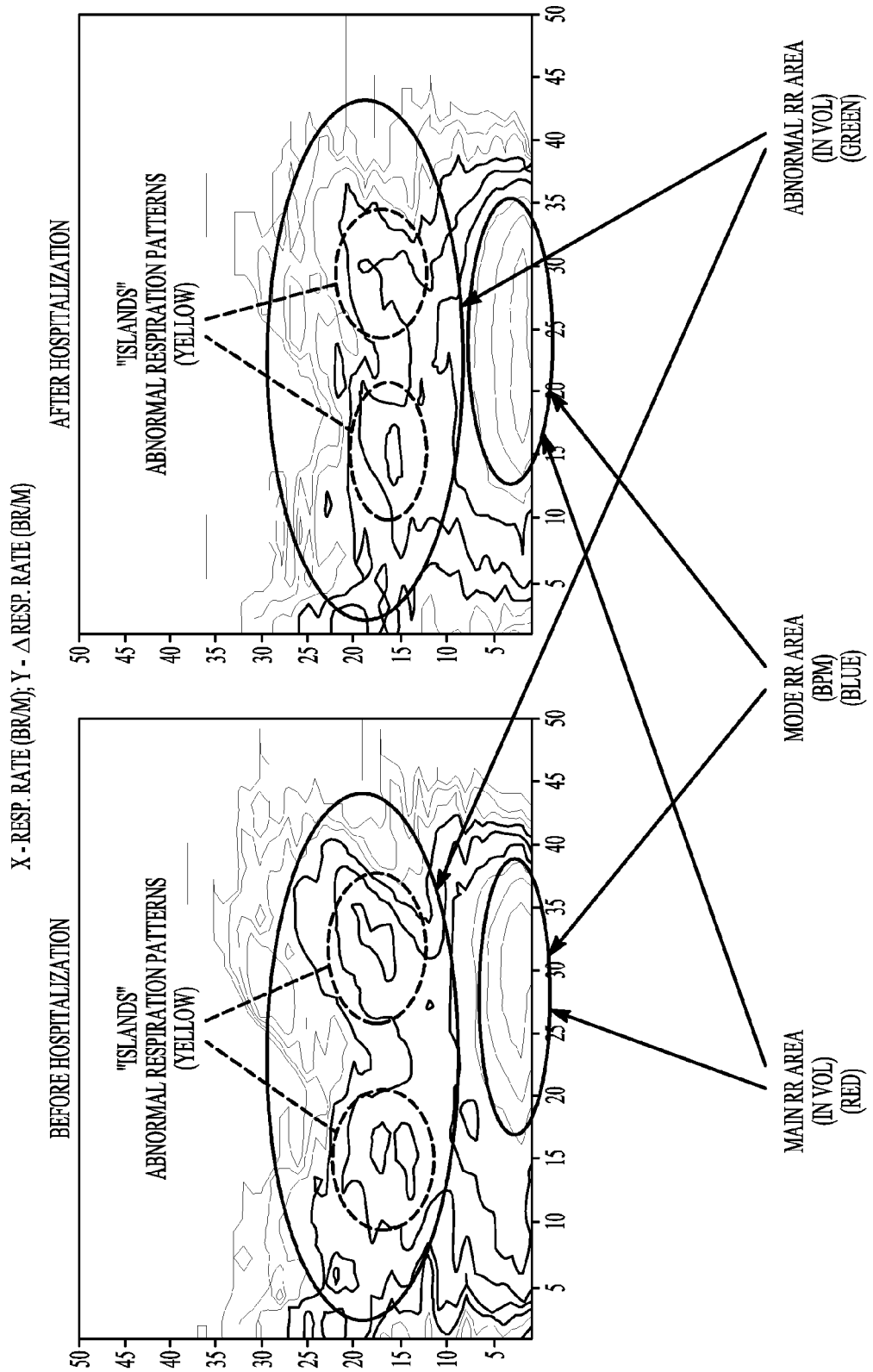
FIG. 10 shows RRV footprints for the same heart failure patient before and after hospitalization, and evidences general improvement in the patient's heart failure status after hospitalization.

FIG. 10 shows RRV footprints for the same heart failure patient before and after hospitalization, and evidences general improvement in the patient's heart failure status after hospitalization. The ectopic "islands" highlighted as yellow regions denoted by dashed ovals are associated with abnormal respiration patterns, such as Cheyne-Stokes Respiration. The RRV footprint developed after patient hospitalization shows a reduction of the island areas, indicating a reduction in Cheyne-Stokes Respiration, for example.

Figure 11:
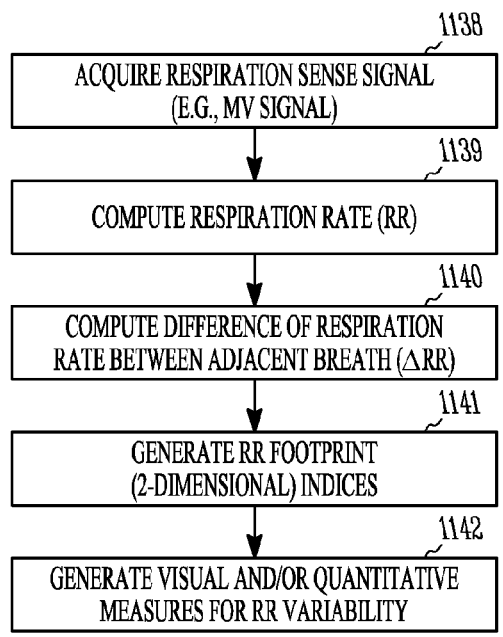
FIG. 11 illustrates an embodiment of a method for determining RRV and generating a footprint of with associated indices.

FIG. 11 illustrates an embodiment of a method for determining respiration rate variability (RRV) and generating a footprint of with associated indices. A respiration sense signal is obtained at 1138 and a respiration rate (RR) is computed using the respiration sense signal at 1139. At 1140, a difference of respiration rate (ΔRR) between adjacent breaths is computed. At 1141, an RR footprint is generated and indices are generated from the footprint. Visual and/or quantitative measures for respiration rate variability are generated 1142. These measures can be used to adjust the intensity of the neural stimulation therapy, such as may be accomplished automatically or through physician intervention.

Figure 12:
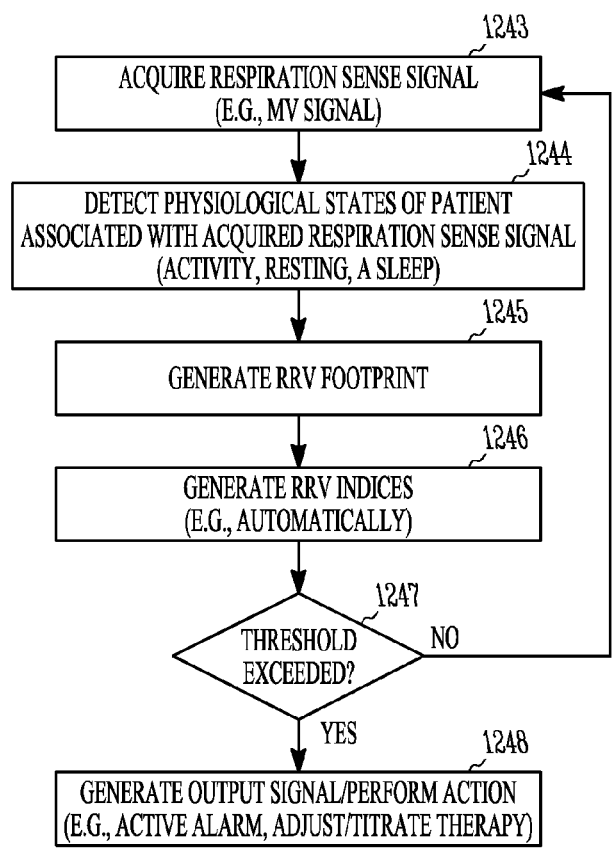
FIG. 12 illustrates an embodiment of a method for determining RRV and generating a footprint of same with associated indices.

FIG. 12 illustrates an embodiment of a method for determining respiration rate variability (RRV) and generating a footprint of same with associated indices. A respiration sense signal is obtained at 1243, such as from a minute ventilation sensor. Physiological states of the patient associated with the respiration sense signal are detected 1244. An RRV footprint is generated 1245 and RRV indices are generated 1246. The RRV indices can be generated automatically or algorithmically. Upon exceeding a threshold 1247, an output, such as an alarm, is generated or some interventional action is performed 1248, such adjustment or titration of a therapy delivered to the patient.

Figure 13:
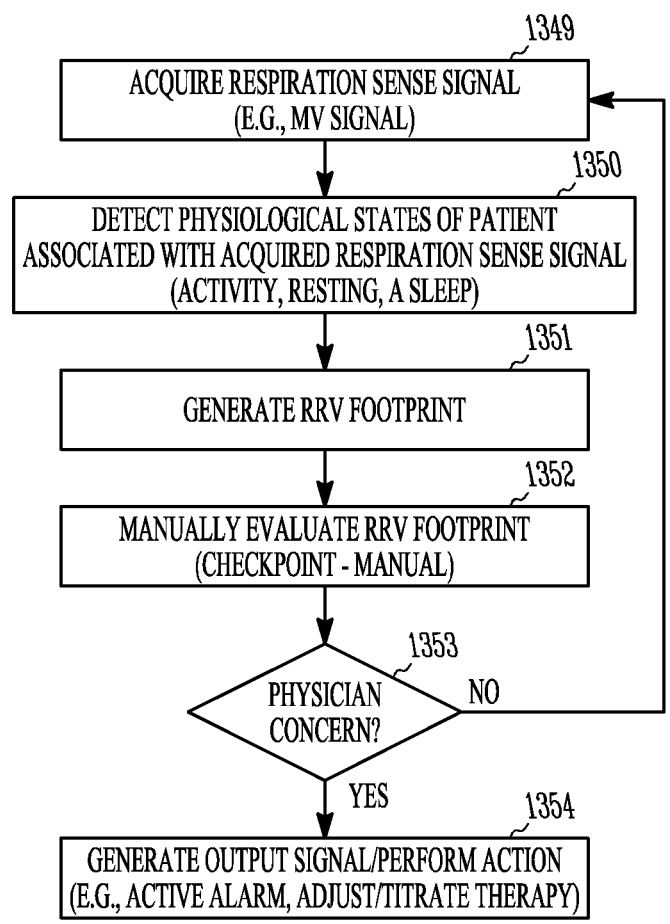
FIG. 13 illustrates an embodiment of a method for determining RRV and generating a footprint of same with associated indices.

FIG. 13 illustrates an embodiment of a method for determining respiration rate variability and generating a footprint of same with associated indices. A respiration sense signal is obtained 1349, such as from a minute ventilation sensor. Physiological states of the patient associated with the respiration sense signal are detected 1350. An RRV footprint is generated 1351. The RRV footprint is evaluated manually 1352, such as by a physician using a display or plot of the RRV footprint presented via a graphical user interface (GUI). The physician may selectively cause the generation of various RRV indices of interest by a processor via the GUI. If the physician is concerned 1353 based on the manual evaluation, the physician may initiate generation of an output, such as an alarm, or some interventional action, such as adjustment or titration of a therapy delivered to the patient 1354.

Figure 14:
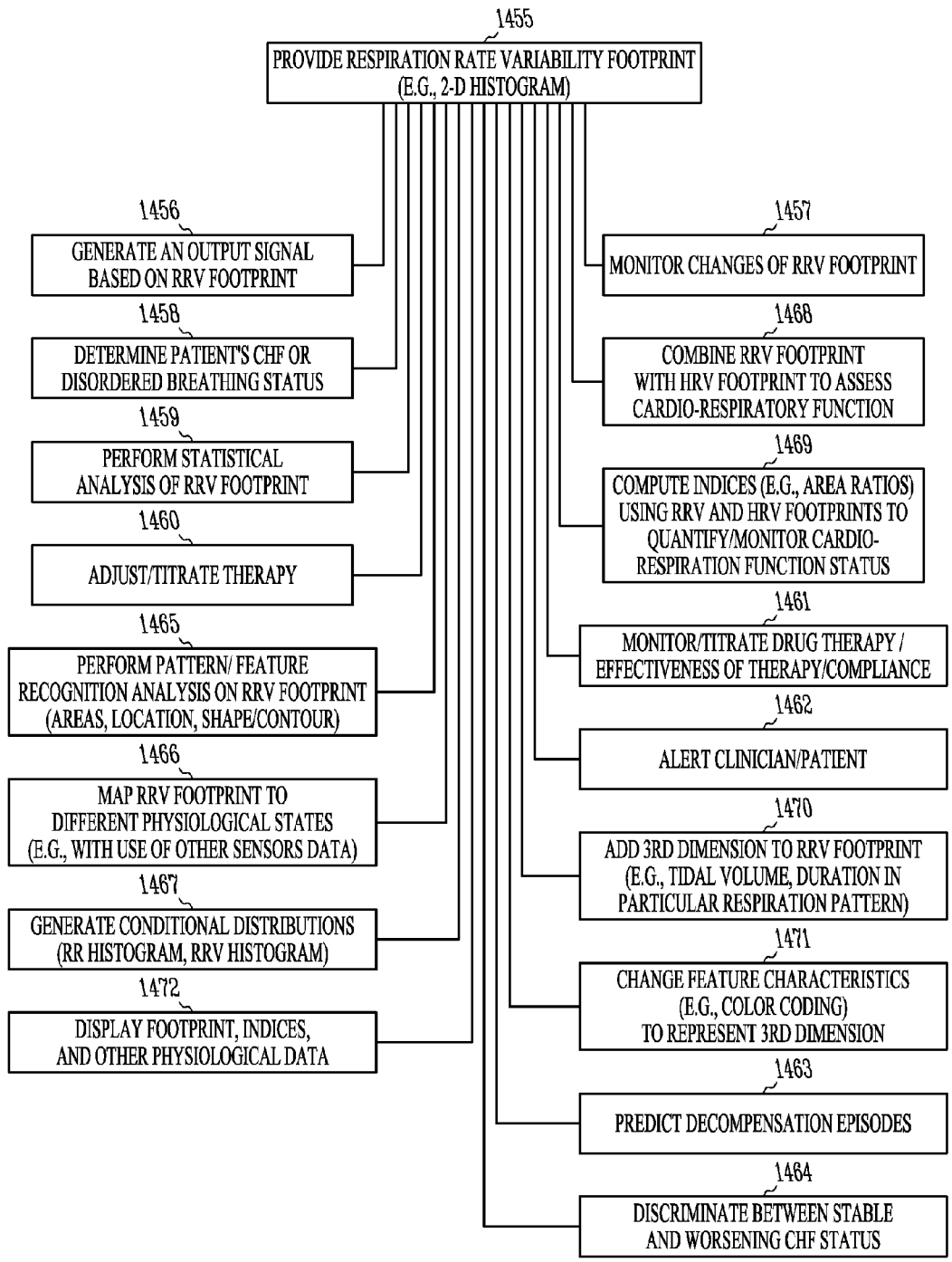
FIG. 14 is a block diagram illustrating a variety of operations that may be performed based on an RRV footprint with associated indices, according to various embodiments.

FIG. 14 is a block diagram illustrating a variety of operations that may be performed based on a respiration rate variability footprint with associated indices 1455, according to various embodiments. A signal based on the RRV footprint may be generated 1456. The signal may take several forms, including an electrical or electromagnetic signal, optical signal, or acoustic signal, for example. This signal may be used for a variety of diagnostic and therapeutic purposes, including titration of a neural stimulation therapy such as a vagal stimulation therapy (VST). The signal may be produced by a medical device implanted within the patient. The signal may be produced by a patient-external device that receives respiration sensor data from a medical device implanted within the patient.

Changes of the RRV footprint may be monitored 1457. Heart failure status, change in heart failure status, disordered breathing status, and/or change is disordered breathing status may be determined and monitored 1458. Various statistical analyses may be performed 1459 on the RRV footprint and associated indices may be computed. Neural stimulation therapy may be monitored and titrated based on the RRV footprint and one or more indices 1460. Effectiveness of the therapy may be quantified using the RRV footprint and associated indices 1461.

An alert to the clinician and/or patient may be generated 1462 and communicated in various forms to the clinician and/or patient based on the RRV footprint and associated indices. The RRV footprint and associated indices may be used to predict decompensation episodes 1463. For example, gradual or sudden changes in a heart failure patient's respiration pattern can be detected from changes in the patient's RRV footprint and associated indices, which can indicate the relative likelihood of a decompensation episode. The RRV footprint and associated indices may be used to discriminate 1464 between stable and worsening heart failure status of a patient.

Pattern and/or feature recognition may be performed 1465 on the RRV footprint, such as for recognizing or identifying areas, locations, shapes/contours of interest that can be associated with particular respiration or patient conditions. Various known pattern and/or feature recognition techniques may be employed, such as by using neural networks and other statistical pattern recognition techniques. Such techniques may include principal component analysis, fisher and variance weight calculations and feature selection. Neural network methods may include a back propagation neural network and/or radial basis function neural network. Statistical pattern recognition, may include linear discriminate analysis, quadratic discriminate analysis, regularized discriminate analysis, soft independent modeling of class analogy, and/or discriminate analysis with shrunken covariance.

An RRV footprint may be mapped 1466 to different physiological states, such as determined by other sensors (e.g., posture sensor, motion sensors). Conditional distributions may be generated 1467 from the RRV footprint. For example, a respiration rate (RR) histogram may be obtained by integrating the RRV footprint along the appropriate axis of the RRV footprint. A respiration rate variability histogram may be obtained by integrating the RRV footprint along the other axis of the RRV footprint.

An RRV footprint may be combined with a heart rate variability (HRV) footprint to provide increased robustness of cardio-respiratory function assessment. A combined RRV and HRV footprint provides for the measurement and tracking of a patient's cardio-respiratory function 1468. Various indices, such as area ratios of the HRV footprint and RRV footprint, may be generated 1469 to quantify a patient's cardio-respiratory function status.

A third dimension may be added to, or superimposed on, the footprint (e.g., two dimensional histogram) 1470. Such third dimension may be tidal volume, a duration of time during which a patient is in a particular respiration pattern or a frequency of occurrence of a particular respiration pattern or rate, for example. The third dimension may be indicated by use of a color scheme 1471 or by a graphical construct or indicia extending from a two dimensional plane of the footprint into a plane orthogonal of this two-dimensional plane.

A variety of RRV footprint and index data, trend data, and other physiological data may be displayed 1472 for use by the patient, clinician, and/or physician. FIG. 14 is intended to provide a non-exhaustive, non-limiting listing of examples concerning the use of an RRV footprint developed using respiration rate data.

Figure 15:
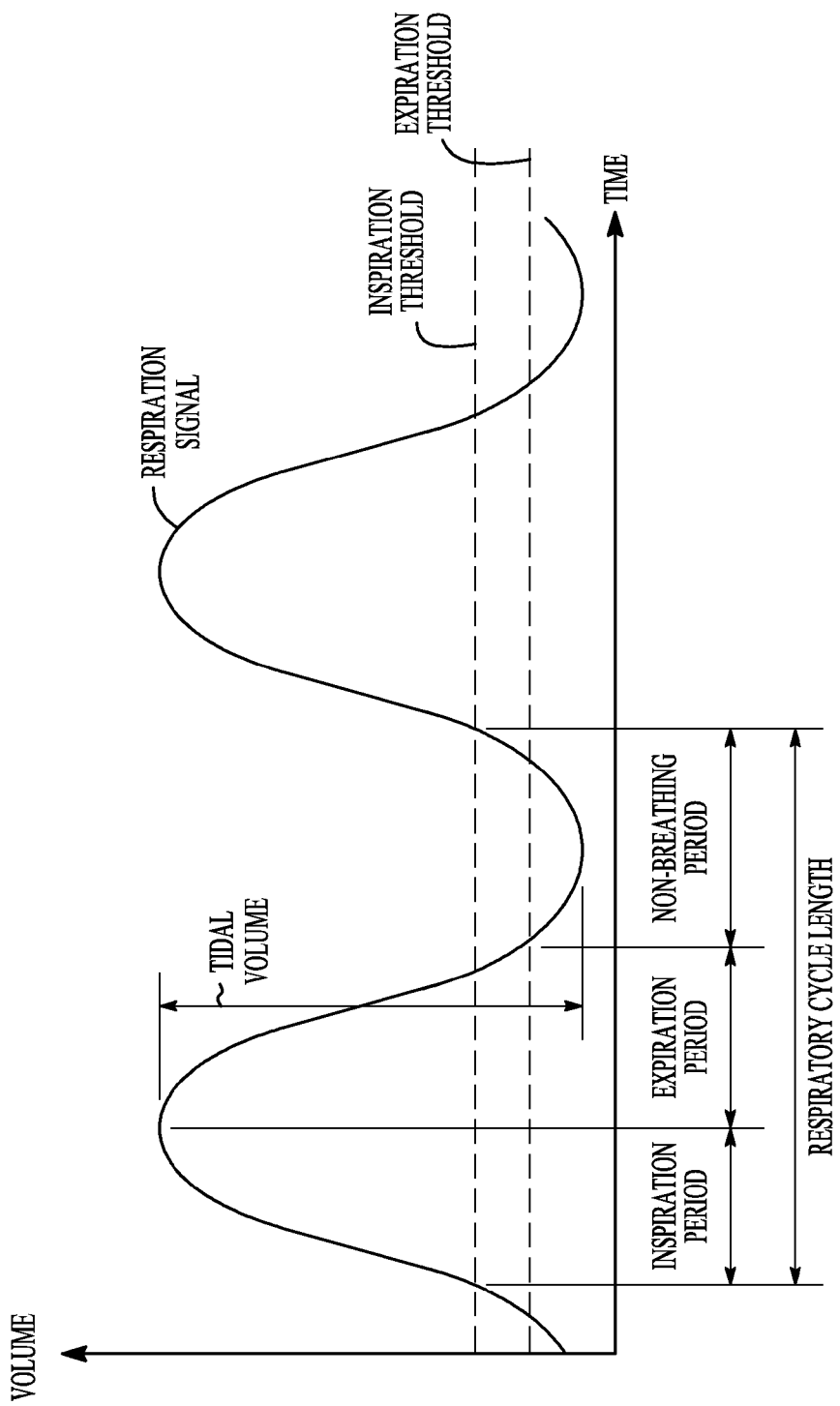
FIG. 15 is an illustration of a respiratory signal indicative of respiratory parameters including respiratory cycle length, inspiration period, expiration period, non-breathing period, and tidal volume.

FIG. 15 is an illustration of a respiratory signal indicative of respiratory parameters including respiratory cycle length, inspiration period, expiration period, non-breathing period, and tidal volume. By way of example, a respiratory variability can be determined using one or more of the parameters illustrated in the figure. The axes of the graph are volume and time, such that the signal represents the respiration volume over time. The inspiration period starts at the onset of the inspiration phase of a respiratory cycle, when the amplitude of the respiratory signal rises above an inspiration threshold, and ends at the onset of the expiration phase of the respiratory cycle, when the amplitude of the respiratory cycle peaks. The expiration period starts at the onset of the expiration phase and ends when the amplitude of the respiratory signal falls below an expiration threshold. The non-breathing period is the time interval between the end of the expiration phase and the beginning of the next inspiration phase. The tidal volume is the peak-to-peak amplitude of the respiratory signal. The respiratory rate can be determined from the cycle length: rate (br/min)=1/(cycle length) when the cycle length is provided in the units of minutes.

The respiratory signal is a physiologic signal indicative of respiratory activities. In various embodiments, the respiratory signal includes any physiology signal that is modulated by respiration. In one embodiment, the respiratory signal is a transthoracic impedance signal sensed by an implantable impedance sensor. In another embodiment, the respiratory signal is extracted from a blood pressure signal that is sensed by an implantable pressure sensor and includes a respiratory component. In another embodiment, the respiratory signal is sensed by an external sensor that senses a signal indicative of chest movement or lung volume.

As provided above, embodiments of the present subject matter detect undesired side effects. One example of an undesired side effect is a respiratory disorder.

Figure 16:
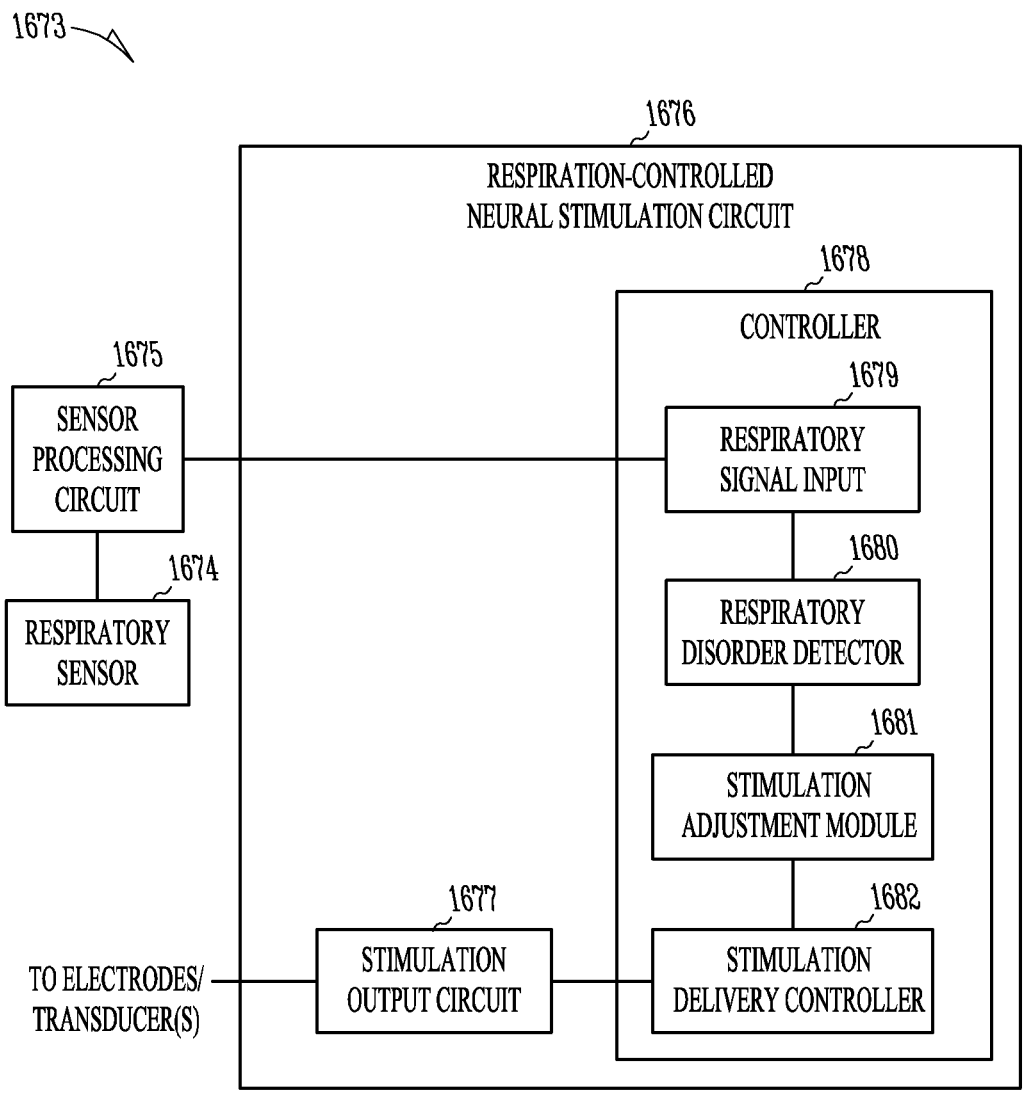
FIG. 16 is a block diagram illustrating an embodiment of a respiratory disorder-responsive neural stimulation system.

FIG. 16 is a block diagram illustrating an embodiment of a respiratory disorder-responsive neural stimulation system. The illustrated system 1673 includes a respiratory sensor 1674, a sensor processing circuit 1675, and a respiration-controlled neural stimulation circuit 1676. The illustrated respiration-controlled neural stimulation circuit 1676 includes a stimulation output circuit 1677 and a controller 1678. The controller 1678 includes a respiratory signal input 1679, a respiratory disorder detector 1680, a stimulation adjustment module 1681, and a stimulation delivery controller 1682. The respiratory disorder detector 1680 detects predetermined-type respiratory disorders using the respiratory signal received by the respiratory signal input 1679. The stimulation adjustment module 1681 adjusts the delivery of the neural stimulation pulses in response to the detection of each of the respiratory disorders. In one embodiment, the stimulation adjustment module 1681 stops the execution of a stimulation algorithm in response to the detection of a respiratory disorder. The stimulation delivery controller 1682 controls the delivery of the neural stimulation pulses by executing one or more stimulation algorithms.

Figure 17:
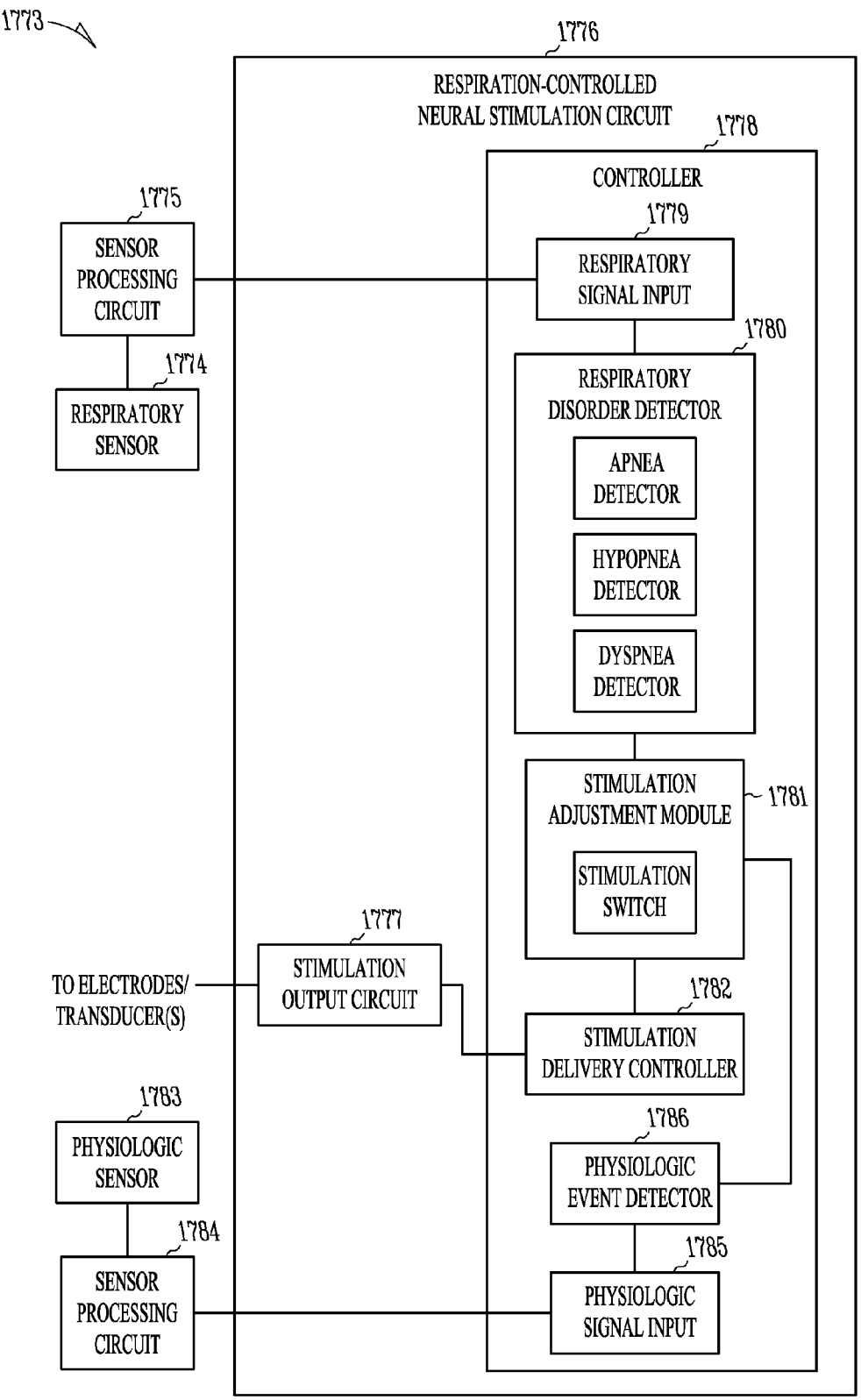
FIG. 17 is a block diagram illustrating an embodiment of a respiratory disorder-responsive neural stimulation system.

FIG. 17 is a block diagram illustrating an embodiment of a respiratory disorder-responsive neural stimulation system 1773. The system 1773 includes a respiratory sensor 1774, a sensor processing circuit 1775, a physiologic sensor 1783, another sensor processing circuit 1784, and a respiration-controlled neural stimulation circuit 1776.

The physiologic sensor 1783 senses one or more physiologic signals in addition to the physiologic signal sensed by respiratory sensor 1774. In various embodiments, the physiologic sensor 1783 senses various combinations of one or more of cardiac signals, signals indicative of heart sounds, cardiac and/or transthoracic impedance signals, signals indicative of blood oxygen level, and signals indicative of nerve traffic. Sensor processing circuit 1784 processes the one or more physiologic signals sensed by physiologic sensor 1783 for use by respiration-controlled neural stimulation circuit 1776 in controlling the neural stimulation. In various embodiments, the physiologic sensor 1783 or portions of physiologic sensor 1783 are included in implantable medical device or communicatively coupled to implantable medical device via one or more leads or telemetry. In various embodiments, the sensor processing circuit 1784 or portions sensor processing circuit 1784 are included in an implantable medical device or communicatively coupled to an implantable medical device via one or more leads or telemetry.

The illustrated respiration-controlled neural stimulation circuit 1776 includes a stimulation output circuit 1777 and a controller 1778. The controller 1778 includes a respiratory signal input 1779, a respiratory disorder detector 1780, a physiologic signal input 1785, a physiologic event detector 1786, a stimulation adjustment module 1781, and a stimulation delivery controller 1782.

The respiratory disorder detector 1780 detects one or more respiratory disorders using the respiratory signal. In the illustrated embodiment, the respiratory disorder detector includes an apnea detector, a hypopnea detector, and a dyspnea detector. In various other embodiments, the respiratory disorder detector includes a combination of one or more of the apnea detector, the hypopnea detector, and the dyspnea detector. In various embodiments, the respiratory disorder detector also detects abnormal values of one or more respiratory parameters, such as a low respiratory rate when the respiratory rate is below a threshold rate, a low tidal volume when the tidal volume is below a detection threshold volume, and a low minute ventilation when the minute ventilation is below a detection threshold value.

Apnea is characterized by abnormally long non-breathing periods. The apnea detector detects apnea by comparing the non-breathing period to a detection threshold period. Apnea is detected when the non-breathing period exceeds the detection threshold period. Hypopnea is characterized by abnormally shallow breathing, i.e., low tidal volume. The hypopnea detector detects hypopnea by comparing the tidal volume to a detection threshold volume. Hypopnea is detected when the tidal volume is below the detection threshold volume. In one embodiment, the tidal volume is an average tidal volume over a predetermined time interval or a predetermined number of respiratory cycles. Dyspnea is characterized by rapid shallow breathing, i.e., high respiratory rate-to-tidal volume ratio. The dyspnea detector detects dyspnea by comparing the ratio of the respiratory rate to the tidal volume to a detection threshold ratio. Dyspnea is detected when the ratio exceeds the threshold ratio. In various embodiments, the threshold period, the detection threshold volume, and/or the threshold ratio are empirically established.

The physiologic signal input receives the one or more physiologic signals sensed by the physiologic sensor and processed by sensor processing circuit. The physiologic event detector detects one or more physiologic events from the one or more physiologic signals. In various embodiments, the physiologic event detector detects one or more of changes in cardiac signal morphology, changes in heart sound waveform morphology, changes in impedance signal morphology, and changes in blood oxygen saturation.

The stimulation adjustment module adjusts the delivery of the neural stimulation pulses in response to at least the detection of a respiratory disorder by the respiratory disorder detector. In one embodiment, the stimulation adjustment module adjusts the delivery of the neural stimulation pulses in response to the detection of a respiratory disorder by the respiratory disorder detector and the detection of a physiologic event by the physiologic event detector. The stimulation delivery controller controls the delivery of the neural stimulation pulses by executing one or more stimulation algorithms. The stimulation adjustment module includes a stimulation switch. The stimulation switch stops executing a first stimulation algorithm in response to the detection of a respiratory disorder such as apnea, hypopnea, or dyspnea. For example, the first stimulation algorithm is executed to treat a cardiac condition by vagal nerve stimulation. If apnea, hypopnea, or dyspnea is detected, the vagal nerve stimulation is to be stopped to avoid the worsening of the condition due to the vagal nerve stimulation designed for treating the cardiac condition.

Figure 18:
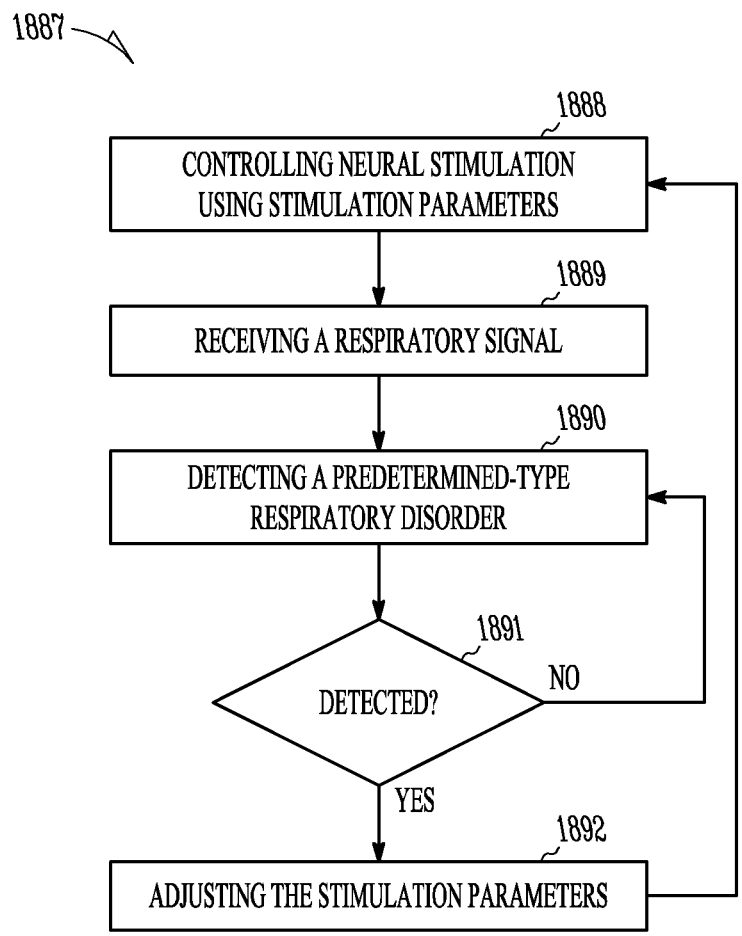
FIG. 18 is a flow chart illustrating an embodiment of a method for adjusting neural stimulation in response to a respiratory disorder.

FIG. 18 is a flow chart illustrating an embodiment of a method for adjusting neural stimulation in response to a respiratory disorder. The method 1887 may be performed by a respiration-controlled neural stimulation circuit. The neural stimulation is controlled by using a plurality of stimulation parameters at 1888. The neural stimulation is delivered to treat a non-respiratory disorder. In one embodiment, neural stimulation is delivered to treat a cardiac condition, such as to treat heart failure or to control cardiac remodeling. A respiratory signal is received at 1889. The respiratory signal is indicative of respiratory cycles and respiratory parameters. Examples of the respiratory parameters include the respiratory cycle length, the inspiration period, the expiration period, the non-breathing period, the tidal volume, and the minute ventilation. In various embodiments, the respiratory signal is, or is derived from, a physiologic signal indicative of the respiratory cycles and the respiratory parameters. Examples of the physiologic signal include a transthoracic impedance signal and blood pressure signals such as a PAP signal. A respiratory disorder is detected at 1890. Examples of the respiratory disorder include abnormal respiratory parameter values such as low respiratory rate, low tidal volume, and low minute ventilation, apnea, hypopnea, and dyspnea. Apnea is detected when the non-breathing period exceeds a detection threshold period. Hypopnea is detected when the tidal volume is below a detection threshold volume. Dyspnea is detected when the ratio of the respiratory rate to the tidal volume exceeds a detection threshold ratio. At 1891, if the respiratory disorder is detected, the neural stimulation is adjusted by adjusting one or more of the stimulation parameters at 1892. The neural stimulation is adjusted to terminate or mitigate the detected respiratory disorder. The neural stimulation can be adjusted to decrease the intensity of the stimulation. The neural stimulation can be suspended for a predetermined period of time or until the respiratory disorder is no longer detected. The neural stimulation can be adjusted to treat the detected respiratory disorder.

According to various embodiments, the device, as illustrated and described above, is adapted to deliver neural stimulation as electrical stimulation to desired neural targets, such as through one or more stimulation electrodes positioned at predetermined location(s). Other elements for delivering neural stimulation can be used. For example, some embodiments use transducers to deliver neural stimulation using other types of energy, such as ultrasound, light, magnetic or thermal energy.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by a processor cause the processor to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable neural stimulator for delivering chronic neural stimulation therapy that includes stimulation of a vagus nerve of a patient, the stimulator comprising:
   at least one respiration sensor configured to be used in monitoring respiration of the patient;
   a neural stimulation therapy delivery module configured to generate a neural stimulation signal for use in stimulating the vagus nerve of the patient for the chronic neural stimulation therapy; and
   a controller operably connected to the at least one respiration sensor and to the neural stimulation therapy delivery module to provide closed-loop therapy control using a marker for efficacy of the chronic neural stimulation therapy in treating a cardiovascular disorder, wherein the controller is configured to:
      control the neural stimulation therapy delivery module, using programmable parameters and a programmed therapy schedule, to deliver the chronic neural stimulation therapy, wherein the chronic neural stimulation therapy is configured to treat the cardiovascular disorder of the patient and is delivered over a period of time that includes a plurality of low activity periods and a plurality of non-low activity periods, wherein the cardiovascular disorder is selected from the group of cardiovascular disorders consisting of heart failure, post myocardial infarction, and hypertension;
      determine the marker for one or more of the plurality of low activity periods during the period of time when the chronic neural stimulation therapy is delivered, wherein in determining the marker the controller is configured to:

receive a respiration signal from the at least one respiration sensor indicative of the patient's respiration;

monitor the respiration signal during one of the plurality of low activity periods within the period of time; and determine a respiration variability measurement over a plurality of respiration cycles for the one of the plurality of low activity periods using the monitored respiration signal, wherein the respiratory variability measurement for the one of the plurality of low activity periods provides the marker for efficacy of the chronic neural stimulation therapy in treating the cardiovascular disorder, wherein the respiration variability measurement includes either a respiration rate variability measurement or a tidal volume variability measurement; and adjust an intensity of the chronic neural stimulation therapy using the determined respiratory variability measurement.

2. The stimulator of claim 1, wherein the controller is configured to:

control the neural stimulation therapy delivery module using programmable parameters;

communicate with and send respiration information indicative of the patient's respiration to an external device to enable the external device to determine the respiration variability measurement using the respiration information; and receive programming instructions from the external device to adjust at least one of the programmable parameters as determined using the respiration variability measurement.

3. The stimulator of claim 1, wherein the controller includes a respiration variability analyzer configured to determine the respiration variability measurement for the one of the plurality of low activity periods using the respiration signal.

4. The stimulator of claim 3, wherein the controller includes a titration detector configured to deliver a control signal to control a therapy intensity of the chronic neural stimulation therapy using the respiration variability measurement for the one of the plurality of low activity periods from the respiration variability analyzer.

5. The stimulator of claim 3, wherein the controller includes a safety detector configured to compare the respiration variability measurement for the one of the plurality of low activity periods from the respiration variability analyzer to a threshold and deliver a control signal to control a therapy intensity of the chronic neural stimulation therapy based on the comparison.

6. The stimulator of claim 1, wherein the one of the plurality of low activity periods is a period of sleep within the period of time when the chronic neural stimulation therapy is delivered.

7. The stimulator of claim 1, further comprising a clock connected to the controller, wherein the controller is configured to control the monitoring of the patient's respiration using the clock according to a predetermined schedule that anticipates periods of low activity within the period of time when the chronic neural stimulation therapy is delivered.

8. The stimulator of claim 1, further comprising an activity sensor connected to the controller, wherein the controller is configured to use the activity sensor to sense periods of low activity within the period of time when the chronic neural stimulation therapy is delivered.

9. A system, comprising:

means for delivering a chronic neural stimulation therapy over a period of time that includes a plurality of low activity periods and a plurality of non-low activity periods to treat a cardiovascular disorder, wherein the cardiovascular disorder is selected from the group of cardiovascular disorders consisting of heart failure, post myocardial infarction, and hypertension, and wherein the means for delivering the chronic neural stimulation therapy is configured to stimulate a vagus nerve;

means for determining a marker for efficacy of the chronic neural stimulation therapy in treating the cardiovascular disorder during one or more of the plurality of low activity periods during the period of time when the chronic neural stimulation therapy is delivered, wherein the means for determining the marker includes:

means for monitoring respiration during one of the plurality of low activity periods within the period of time; and means for determining a respiration variability over a plurality of respiration cycles for the one of the plurality of low activity periods using the monitored respiration, wherein the respiratory variability measurement for the one of the plurality of low activity periods provides a marker for efficacy of the chronic neural stimulation therapy in treating the cardiovascular disorder, wherein the respiration variability measurement includes either a respiration rate variability measurement or a tidal volume variability measurement; and means for adjusting an intensity of the stimulation to the vagus nerve if the respiration variability measurement crosses a predetermined threshold to provide closed-loop therapy control.

10. The system of claim 9, wherein the means for monitoring respiration during one of the plurality of low activity periods includes means for monitoring respiration variability during sleep.

11. The system of claim 9, wherein the means for adjusting includes means for adjusting the intensity of the stimulation to the vagus nerve based on a comparison of the respiration variability measurement for the one of the plurality of low activity periods to a predetermined titration threshold indicative of the efficacy of the chronic neural stimulation therapy in treating the cardiovascular disorder.

12. The system of claim 9, wherein the means for adjusting includes means for adjusting the intensity of the stimulation to the vagus nerve based on a comparison of the respiration variability measurement for the one of the plurality of low activity periods to a predetermined side effect threshold indicative of an undesired side effect of the simulation for the therapy.

13. A method, comprising:

delivering a chronic neural stimulation therapy over a period of time that includes a plurality of low activity periods and a plurality of non-low activity periods to treat a cardiovascular disorder selected from the group of cardiovascular disorders consisting of heart failure, post myocardial infarction, and hypertension, wherein delivering the chronic neural stimulation therapy includes delivering stimulation to a vagus nerve;

determining a marker for efficacy of the chronic neural stimulation therapy in treating the cardiovascular disorder for one or more of the plurality of low activity periods during the period of time when the chronic neural stimulation therapy is delivered, wherein determining the marker includes:

monitoring respiration during one of the plurality of low activity periods within the period of time; and determining a respiration variability measurement over a plurality of respiration cycles for the one of the plurality of low activity periods using the monitored respiration, wherein the respiratory variability measurement for the one of the plurality of low activity periods provides a marker for efficacy of the chronic neural stimulation therapy in treating the cardiovascular disorder, wherein the respiration variability measurement includes either a respiration rate variability measurement or a tidal volume variability measurement; and adjusting an intensity of the stimulation to the vagus nerve using a comparison of the respiration variability measurement to at least one predetermined threshold to provide closed-loop therapy control.

14. The method of claim 13, wherein the at least one predetermined threshold includes a titration threshold indicative of the efficacy of the chronic neural stimulation therapy in treating the cardiovascular disorder.

15. The method of claim 13, wherein the at least one predetermined threshold includes a side effect threshold indicative of an undesired side effect of the stimulation.

16. The method of claim 13, further comprising determining if a respiratory disorder is reflected by the monitored respiration, and adjusting the intensity of the stimulation to the vagus nerve if the monitored respiration reflects the respiratory disorder.

17. The method of claim 16, wherein determining if a respiratory disorder is reflected by the monitored respiration includes determining if a respiratory disorder is reflected by the determined respiration variability measurement.

18. The method of claim 13, further comprising adjusting the intensity of the stimulation to the vagus nerve using a comparison of the monitored respiration to a predetermined side effect threshold.

19. The method of claim 13, wherein adjusting the intensity of the stimulation includes adjusting the intensity of the stimulation using a comparison of the determined respiration variability measurement to a predetermined side effect threshold.

20. The method of claim 13, further comprising identifying a patient indicated for a heart failure therapy and delivering the chronic neural stimulation therapy for the patient indicated for the heart failure therapy, wherein the chronic neural stimulation therapy includes a heart failure therapy.

21. The method of claim 13, further comprising identifying a patient indicated for a hypertension therapy and delivering the chronic neural stimulation therapy for the patient indicated for the hypertension therapy, wherein the chronic neural stimulation therapy includes a hypertension therapy.

22. The method of claim 13, further comprising identifying a patient indicated for a post myocardial infarction therapy and delivering the chronic neural stimulation therapy for the patient indicated for the post myocardial infarction therapy, wherein the chronic neural stimulation therapy includes a post myocardial infarction therapy.

23. The method of claim 13, wherein the respiration variability measurement includes the respiration rate variability measurement.

24. The method of claim 13, wherein the respiration variability measurement includes the tidal volume variability measurement.

25. The method of claim 13, wherein determining respiration variability for the one of the plurality of low activity periods includes generating a footprint representative of the respiration variability for the one of the plurality of low activity periods, and generating one or more indices representative of quantitative measurements of the footprint, wherein generating the footprint includes measuring a respiration parameter at a plurality of times during the one of the plurality of low activity periods to provide a plurality of measured values for the respiratory parameter during the one of the plurality of low activity periods, determining changes between the measured values, and associating the changes to the values of the measured parameters.

26. The method of claim 25, wherein the one or more indices includes a feature, a pattern, a shape or a contour of the footprint.

* * * * *